United States Patent
Yarimizu et al.

(10) Patent No.: US 8,247,470 B2
(45) Date of Patent: Aug. 21, 2012

(54) POLYMERIZABLE COMPOSITION

(75) Inventors: Hideki Yarimizu, Itabashi-ku (JP);
Hideki Tokui, Itabashi-ku (JP); Hiroto Minamisawa, Itabashi-ku (JP)

(73) Assignee: GC Corporation, Tokyo (JP)

( * ) Notice: Subject to any disclaimer, the term of this patent is extended or adjusted under 35 U.S.C. 154(b) by 100 days.

(21) Appl. No.: 12/728,711

(22) Filed: Mar. 22, 2010

(65) Prior Publication Data

US 2010/0249266 A1    Sep. 30, 2010

(30) Foreign Application Priority Data

Mar. 25, 2009    (JP) ................. 2009-074842

(51) Int. Cl.
*A61K 6/083* (2006.01)
*C08K 3/40* (2006.01)
(52) U.S. Cl. ............. 523/116; 523/118; 433/228.1
(58) Field of Classification Search .......... 523/116, 523/118; 524/494; 433/228.1
See application file for complete search history.

(56) References Cited

U.S. PATENT DOCUMENTS

| | | | | |
|---|---|---|---|---|
| 4,343,921 A * | 8/1982 | Piestert | ........... | 525/310 |
| 2002/0039957 A1 * | 4/2002 | Kobayashi et al. | ........... | 501/20 |
| 2004/0235981 A1 | 11/2004 | Qian | | |
| 2007/0088097 A1 | 4/2007 | Qian | | |
| 2009/0048364 A1 * | 2/2009 | Liu | ........... | 522/48 |
| 2010/0068540 A1 | 3/2010 | Hisha et al. | | |
| 2011/0046256 A1 | 2/2011 | Yarimizu et al. | | |

FOREIGN PATENT DOCUMENTS

| | | |
|---|---|---|
| JP | 58-219281 A | 12/1983 |
| JP | 63-27505 A | 2/1988 |
| JP | 2003-105008 A | 4/2003 |
| JP | 2006-188627 A | 7/2006 |
| JP | 2007-56020 A | 3/2007 |
| JP | 2009144054 A * | 7/2009 |
| WO | WO 2008/108273 A1 | 9/2008 |

OTHER PUBLICATIONS

Extended European Search Report issued May 31, 2010, in Patent Application No. 10002962.8-1214.

* cited by examiner

*Primary Examiner* — Tae H Yoon
(74) *Attorney, Agent, or Firm* — Oblon, Spivak, McClelland, Maier & Neustadt, L.L.P.

(57) ABSTRACT

To provide a polymerizable composition having more excellent preservation stability of pastes than a conventional composition using a combination of a copper compound, cumene hydroperoxide, and N-acetylthiourea, and having a polymerization curing time which does not change with time, that is, does not delay or quicken from a time set for a product even though the composition is stored, the polymerizable composition includes a first paste and a second paste, wherein the first paste includes a polymer of α-β unsaturated monocarboxylic acid or α-β unsaturated dicarboxylic acid, water, and a hydroperoxide as a peroxide, and the second paste includes a (meth)acrylate compound not having an acid group, fluoroaluminosilicate glass powder, a thiourea derivative as a reducing material, and a vanadium compound as a polymerization accelerator.

20 Claims, No Drawings

POLYMERIZABLE COMPOSITION

CROSS-REFERENCE TO RELATED APPLICATIONS

This application is based upon and claims the benefit of priority from prior Japanese Patent Application No. 2009-074842, filed on Mar. 25, 2009.

BACKGROUND OF THE INVENTION

1. Field of the Invention

The present invention relates to a polymerizable composition particularly used for a dental treatment.

2. Description of the Conventional Art

The present invention relates to a polymerizable composition used by mixing two kinds of pastes. More particularly, the present invention relates to the polymerizable composition that even though each of the pastes before polymerization is stored for a long period of time without being refrigerated, the polymerizable composition does not gelate and a curing time of the polymerizable composition does not change with time. Furthermore, the polymerizable time does not delay or quicken even though the polymerizable composition is stored.

A method of combining an organic peroxide and an aromatic tert-amine and using the mixture as a chemical polymerization catalyst has been conventionally used for mixing and polymerizing polymerizable compositions at ordinary temperature, where the polymerizable compositions include a monomer, an oligomer, and a prepolymer of acrylate, a methacrylate and the like which have radical polymerization property. This method can control a time of polymerization and can increase preservation stability of the composition before polymerization by adjusting an amount of the organic peroxide blended with a first paste and an amount of the aromatic tert-amine blending with a second paste, and together using a polymerization inhibitor. However, the polymerizable composition has a problem that a cured body after polymerization is discolored while time passes by the aromatic tert-amine. In addition, the organic peroxide is unstable. Thus, when a great amount of the organic peroxide blends with the paste of the polymerizable composition and the paste is stored for a long period of time, the paste tend to gelate before polymerization. By contrast, when a great amount of the polymerization inhibitor blends with the paste in order to secure long-term preservation stability, a polymerization time comes to be too long. Therefore, the conventional polymerizable composition should be refrigerated and stored for regulate the reaction of the organic peroxide.

As another chemical polymerization catalyst, a composition is obtained by combining an organic aromatic compound including at least one $—SO_2—$ group, a peroxide, and an aromatic tert-amine. However, since the organic peroxide and the aromatic tert-amine are used, there are still problems that a cured body discolors and preservation stability is low.

Further, a polymerization method using trialkylborane is also known. However, trialkylborane has a disadvantage that trialkylborane cannot previously blend with the polymerizable composition including a (meth)acrylate compound having radical polymerization property since trialkylborane is oxidized easier than aromatic tert-amine. Therefore, trialkylborane should be stored in a vessel separating from the (meth)acrylate compound, and should be added to the polymerizable composition at each use. Thus, an operation is complicated.

The present inventors developed before a composition including a ternary catalyst including a pyrimidinetrione derivative, an organohalogen compound, and an organometallic compound, and filed a patent application for this composition under Japanese Patent Application Laid-Open No. 2003-105008. Since this composition does not include amine, a cured body does not discolor, and the composition can be used under acid conditions. However, the ternary catalyst still has a problem in preservation stability of the pyrimidinetrione derivative.

In addition to this, for example, Japanese Patent Application Laid-Open No. 58-219281 discloses a combination of cumene hydroperoxide and a thiourea derivative. This combination has better stability to higher temperature than that of conventional ones. However, a polymerizable composition using the combination has a problem that a curing reaction generated by cumene hydroperoxide and a thiourea derivative is slow. Even if a blending concentration is sufficient, a polymerization speed which is appropriate for dental adhesives cannot be obtained.

In order to improve this composition, for example, Japanese Patent Application Laid-Open No. 2007-056020 discloses a combination of cumene hydroperoxide and N-acetylthiourea, which is obtained by a redox reaction under the existence of a copper compound. Since this combination has comparatively high thermal stability and does not include an aromatic tert-aimine, a cured body does not discolor with time. Further, this combination is characterized in that it is not influenced by acid of a (meth)acrylate compound having an acid group, which is conventionally blended in order to give adhesive property to a polymerizable composition. Thus, the composition has excellent preservation stability. However, when an operator adheres a dental prosthesis to a tooth, a dental material is required to have property that the material is cured suitably within a time desired by an operator, and to be constant in a curing time for every product. Any of the combinations mentioned above still does not satisfy the requirements of stability of the curing time.

SUMMARY OF THE INVENTION

Problem to be Solved by the Invention

The present invention is directed to a polymerizable composition having more excellent preservation stability of pastes than conventional compositions using a combination of a copper compound, cumene hydroperoxide, and N-acetylthiourea, and having a curing time which does not change with time, that is, does not delay or quicken from the initial value even though the composition is stored.

Means for Solving the Problem

Present inventors carried out earnest works to solve the aforementioned problems, and as a result, they found out the followings to complete the present invention. A polymerizable composition having excellent curability and excellent preservation stability can be produced by using a hydroperoxide as a peroxide, using a thiourea derivative as a reducing material, and using a vanadium compound as an accelerator.

The present invention is a polymerizable composition including a first paste and a second paste. The first paste includes a polymer of α-β unsaturated monocarboxylic acid or α-β unsaturated dicarboxylic acid, water, and a hydroperoxide as a peroxide. The second paste includes a (meth)acrylate compound, fluoroaluminosilicate glass powder, a thiourea derivative as a reducing material, and a vanadium compound as a polymerization accelerator. Preferably, in the polymerizable composition, the thiourea derivative is one or more kinds selected from ethylenethiourea, diethylthiourea, tetramethylthiourea, N-acetylthiourea, N-benzoylthiourea, diphenylthioura, and dicyclohexylthiourea, and the vanadium compound is one or more kinds selected from vanadium acetylacetonate, vanadyl acetylacetonate, vanadyl stearate, vanadium naphthenate, and vanadium benzoyl acetonate.

Effect of the Invention

The polymerizable composition according to the present invention has more excellent preservation stability than a conventional composition using a combination of a copper compound, cumene hydroperoxide and N-acetylthiourea.

DETAILED DESCRIPTION OF PREFERRED EMBODIMENT

The polymer of α-β unsaturated monocarboxylic acid or α-β unsaturated dicarboxylic acid used in the present invention is a copolymer or a homopolymer including one or more kinds selected from acrylic acid, methacrylic acid, 2-chloroacrylic acid, 3-chloroacrylic acid, aconitic acid, mesaconic acid, maleic acid, itaconic acid, fumaric acid, glutaconic acid, and citraconic acid. The blending amount of the polymer of α-β unsaturated monocarboxylic acid or α-β unsaturated dicarboxylic acid is preferably 10 to 60% by weight in the first component. Preferably, the polymer does not include a polymerizable ethylenic unsaturated double bond, and does have a weight-average molecular weight of 5,000 to 40,000. If the weight-average molecular weight is less than 5,000, the strength of a cured body easily decreases, and an adhesive strength to the tooth tends to decrease. If the weight-average molecular weight is more than 40,000, a viscosity at a time of kneading is too high, so that the kneading comes to be difficult.

The polymerizable composition according to the present invention includes water in the first component. Preferably, the blending amount of water is 10 to 60% by weight in the first component. The polymerizable composition according to the present invention utilize two kinds of setting mechanisms, which are a polymerization reaction of a (meth) acrylate compound and a reaction of the polymer of α-β unsaturated monocarboxylic acid or α-β unsaturated dicarboxylic acid with fluoroaluminosilicate glass powder under the existence of the water.

A polymerization reaction used for the polymerizable composition according to the present invention uses an oxidation-reduction reaction of a hydroperoxide and a thiourea derivative. In the first paste, a hydroperoxide as a peroxide material is blended. In the second paste, a thiourea derivative as a reducing material and a vanadium compound as an accelerator are blended.

The blending amount of the hydroperoxide in the first paste is preferably 0.01 to 10% by weight. If the blending amount is less than 0.01% by weight, the function as a redox polymerization initiator tends to be insufficient. If the blending amount is more than 10% by weight, the polymerization speed at the use of mixing the first paste and the second paste is too high, so that it is unpractical. The hydroperoxide could be p-menthane hydroperoxide, diisopropylbenzene hydroperoxide, 1,1,3,3-butyl hydroperoxide, cumene hydroperoxide, tert-butyl hydroperoxide, or the like. Particularly, cumene hydroperoxide and tert-butyl hydroperoxide are preferable due to the reason of preservation stability.

The second component includes fluoroaluminosilicate glass powder as mentioned below and a (meth)acrylate compound not having an acid group. The (meth)acrylate compound means various kinds of monomers, oligomers, and prepolymers of acrylate or methacrylate. More particularly, the (meth)acrylate compound not having an acid group in the present invention could be methyl(meth)acrylate, ethyl (meth)acrylate, isopropyl(meth)acrylate, n-butyl(meth)acrylate, isobutyl(meth)acrylate, hydroxypropyl(meth)acrylate, tetrahydrofurfryl(meth)acrylate, glycidyl(meth)acrylate, 2-hydroxyethyl(meth)acrylate, 2-hydroxypropyl(meth)acrylate, 3-hydroxypropyl(meth)acrylate, 2-methoxyethyl(meth)acrylate, 2-ethoxyethyl(meth)acrylate, 2-methoxyethyl (meth)acrylate, 2-ethylhexyl(meth)acrylate, benzyl(meth) acrylate, 2-hydroxy-1,3-di(meth)acryloxy propane, ethylene glycol di(meth)acrylate, diethylene glycol di(meth)acrylate, triethylene glycol di(meth)acrylate, butylene glycol di(meth) acrylate, neopentyl glycol di(meth)acrylate, 1,3-butanediol di(meth)acrylate, 1,4-butanediol di(meth)acrylate, 1,6-hexanediol di(meth)acrylate, trimethylolpropane tri(meth)acrylate, trimethylolethane tri(meth)acrylate, pentaerythritol tri (meth)acrylate, trimethylolmethane tri(meth)acrylate, pentaerythritol tetra(meth)acrylate, polybutylene glycol di(meth)acrylate, or bisphenol A glycidyl (meth)acrylate. A monomer, oligomer, and prepolymer of these compounds can be properly used. Further, as for (meth)acrylate having urethane bond, di-2-(meth)acryloxyethyl-2,2,4-trimethylhexamethylene dicarbamate, 1,3,5-tris[1,3-bis{(meth)acryloyloxy}-2-propoxycarbonylaminohexane]-1,3,5-(1H,3H,5H) triazine-2,4,6-trione, and 2,2-bis-4-(3-(meth)acryloyloxy-2-hydroxypropyl)-phenylpropane, can be used. In addition, the (meth)acrylate having urethane bond could be (meth)acrylate of urethane oligomer including 2,2'-di(4-hydroxycyclohexyl) propane, 2-oxypanone, hexamethylene diisocyanate, and 2-hydroxyethyl(meth)acrylate, and (meth)acrylate of urethane oligomer including 1,3-butanediol, hexamethylene diisocyanate, and 2-hydroxyethyl(meth)acrylate. These can be used independently or by mixing two or more kinds.

The fluoroaluminosilicate glass powder is used for giving X-ray imaging property to a kneaded material. In addition, the fluoroaluminosilicate glass power sets by reacting with the polymer of α-β unsaturated monocarboxylic acid or α-β unsaturated dicarboxylic acid under the existence of water. The fluoroaluminosilicate glass powder includes $Al^{3+}$, $Si^{4+}$, $F^-$, and $O^{2-}$, as primary components, and preferably, further includes $Sr^{2+}$ and/or $Ca^{2+}$. Particularly, as for the preferable ratio of the primary components with respect to the total weight, $Al^{3+}$ is 10 to 21% by weight, $Si^{4+}$ is 9 to 21% by weight, $F^-$ is 1 to 20% by weight, and the total of $Sr^{2+}$ and $Ca^{2+}$ is 10 to 34% by weight. The fluoroaluminosilicate glass powder can be treated with a silane coupling agent, like a filler mentioned below.

The thiourea derivative is a reducing material for redox polymerization. The content of the thiourea derivative in the second paste is preferably 0.01 to 10% by weight. If the content is less than 0.01% by weight, the ability as a polymerization catalyst is insufficient. If the content is more than 10% by weight, a curing time is hard to stabilize. The thiourea derivative could be ethylenethiourea, diethylthiourea, tetramethylthiourea, N-acetylthiourea, N-benzoylthiourea, diphenylthiourea, dicyclohexylthiourea, or the like. Particularly, N-acetylthiourea and N-benzoylthiourea are preferable.

The vanadium compound is a polymerization accelerator for redox polymerization. The blending amount of the vanadium compounds in the second paste is preferably 0.001 to 1% by weight. If the blending amount is less than 0.001% by weight, the effect as the polymerization accelerator tends to be insufficient. If the blending amount is more than 1% by weight, the polymerization at the time of mixing the first paste and the second paste to use the mixture is too rapid, so that it is unpractical. The vanadium compound could be vanadium acetylacetonate, vanadyl acetylacetonate, vanadyl stearate, vanadium naphthenate, vanadium benzoyl acetonate, or the like. Particularly, vanadium acetylacetonate and vanadyl acetylacetonate are preferable.

The polymerizable composition according to the present invention can include a (meth)acrylate compound not having an acid group in the first paste.

The polymerizable composition according to the present invention can include a filler other than the fluoroaluminosilicate glass powder, in the first component and/or the second paste. The filler component has an effect to increase the strength of the composition. The filler could be powder of anhydrous silicic acid, glasses such as barium glass, alumina glass, potassium glass and the like, synthetic zeolite, calcium phosphate, feldspar, fumed silica, aluminum silicate, calcium silicate, magnesium carbonate, hydrous silicic acid, hydrous calcium silicate, hydrous aluminum silicate, quartz, or the like. In order to bond with (meth)acrylate compound, the filler can be treated with a silane coupling agent, such as γ-methacryloxypropyltrimethoxysilane, vinyltrichlorosilane, vinyltriethoxysilane, vinyltrimethoxysilane, vinyltriacetoxysilane, vinyltri(methoxyethoxy)silane, or the like. Further, an pre-polymerized filler produced by previously mixing the aforementioned filler with a monomer and/or an oligomer, curing the mixture, and pulverizing the cured body, can be used. These fillers are used independently or by mixing two or more. Particularly, anhydrous silicic acid, hydrous silicic acid, hydrous calcium silicate, and hydrous aluminum silicate have an effect for preventing the polymerizable composition before polymerization from gelling even when being stored for a long period of time.

The mixing ratio of the first paste and the second paste in the polymerizable composition according to the present invention is preferably 10:1 to 1:10 by weight. If the ratio is out of this range, the balance of each of the polymerization catalysts becomes hard to keep, so that some problems in polymerization could occur.

In addition, the polymerizable composition according to the present invention can properly include a photopolymerization catalyst, an antibacterial, a pigment, and the like, which are conventionally used, if necessary.

EXAMPLES

First pastes and second pastes were produced with the blending ratio (% by weight) illustrated in Tables 2 to 5, and these were subjected to a test for preservation stability.

Brevity codes in the tables are as follows.
TEGDMA: Triethylene glycol dimethacrylate
UDMA: Di-2-methacryloxyethyl-2,2,4-trimethylhexamethylene dicarbamate
HEMA: 2-hydroxy methacrylate
MDP: 10-(meth)acryloyloxydecyldihydrogen phosphate
Aerosil: Fumed silica (the product name: R812, produced by Nippon Aerosil Corporation)
BPO: Benzoyl peroxide
DAC: Dimethyl ammonium chloride
BHT: Butylhydroxytoluene
p-amine: p-tolyldiethanolamine
N-C5EPT: N-cyclohexyl 5 ethylpyrimidinetrione
AACu: Acetylacetone copper The blending ratio of the fluoroaluminosilicate glass powder is illustrated in Table 1.

TABLE 1

|  | Fluoroaluminosilicate glass powder | | |
|---|---|---|---|
|  | FG I | FG II | FG III |
| Aluminum oxide (g) | 21 | 23 | 22 |
| Anhydrous silicic acid (g) | 44 | 41 | 43 |
| Calcium fluoride (g) | 12 | 10 | 12 |
| Calcium phosphate (g) | 14 | 13 | 15 |
| Strontium carbonate (g) | 9 | 13 | 8 |

The fluoroaluminosilicate glass powder was produced by fully mixing raw materials, putting the mixture in a high temperature electric furnace at 1200° C. for 5 hours so as to fuse a glass, cooling the fused glass rapidly, pulverizing the glass for 10 hours using a ball mill, and passing the pulverized glass through a 200 mesh shive (ASTM).

[Test for Confirming Preservation Stability]

In each of examples and comparative examples, the polymerizable composition was stored in a constant temperature container at 23° C. and 50° C., and curing times were measured at a time of producing the composition and a time of 12 weeks later. In a constant temperature room at 23±1° C., the first paste of 2 g and the second paste of 2 g were weighed, taken on a kneading paper, and uniformly mixed by a manual kneading operation using a spatura for 15 seconds. An exothermic curve of the polymerizable composition was measured based on ISO4029:2000 7.6. A reading method of the curing time was based on ISO4029:2000 7.8. These results were illustrated in Tables 6 and 7.

Clearly from Tables 6 and 7, it was confirmed that the curing time of the polymerizable composition including a hydroperoxide, a thiourea derivative, and a vanadium compound initiator did not delay a lot, regardless of the different composition of a (meth)acrylate compound conventionally used for a dental material, and regardless of the existence of a (meth)acrylate compound having an acid group.

TABLE 2

|  |  |  | Example 1 | Example 2 | Example 3 | Example 4 | Example 5 | Example 6 |
|---|---|---|---|---|---|---|---|---|
| First Paste | Hydroperoxide | p-Menthane hydroperoxide | 1 | 2 |  |  |  |  |
|  |  | Cumene hydroperoxide |  |  | 1 | 2 |  |  |
|  |  | tert-Butylhydroperoxide |  |  |  |  | 1 | 2 |
|  | Polymer of α-β unsaturated monocarboxylic | Polycarboxylic acid | 34 | 34 | 20 | 20 | 20 | 20 |

TABLE 2-continued

|  |  | Example 1 | Example 2 | Example 3 | Example 4 | Example 5 | Example 6 |
|---|---|---|---|---|---|---|---|
| acid or α-β unsaturated dicarboxylic acid |  |  |  |  |  |  |  |
| Water |  | 65 | 64 | 35 | 35 | 35 | 35 |
| Filler | Crystalline quartz |  |  | 40 | 39 |  |  |
|  | Amorphosized quartz |  |  |  |  | 40 | 39 |
|  | Aerosil |  |  | 4 | 4 | 4 | 4 |

TABLE 3

|  |  |  | Example 1 | Example 2 | Example 3 | Example 4 | Example 5 | Example 6 |
|---|---|---|---|---|---|---|---|---|
| Second paste | Thiourea Derivative | N-Acetylthiourea | 0.25 | 0.5 |  |  |  |  |
|  |  | N-Benzoylthiourea |  |  | 0.25 | 0.5 |  |  |
|  |  | Diphenylthiourea |  |  |  |  | 0.25 | 0.5 |
|  | Vanadium Compound | Vanadium acetylacetonate | 0.05 | 0.05 |  |  |  |  |
|  |  | Vanadyl acetylacetonate |  |  | 0.05 | 0.05 |  |  |
|  |  | Vanadyl stearate |  |  |  |  | 0.05 | 0.05 |
|  | (Meth) acrylate | UDMA | 3 | 3 | 3 | 3 | 3 | 3 |
|  |  | TEGDMA | 3 | 3 | 3 | 3 | 3 | 3 |
|  |  | HEMA | 20 | 20 | 20 | 20 | 20 | 20 |
|  | Filler | FG I | 69 | 69 |  |  |  |  |
|  |  | FG II |  |  | 69 | 69 |  |  |
|  |  | FG III |  |  |  |  | 69 | 69 |
|  |  | Aerosil | 4.5 | 4.25 | 4.5 | 4.25 | 4.5 | 4.25 |
|  | Other | Camphorquinone | 0.2 | 0.2 | 0.2 | 0.2 | 0.2 | 0.2 |

TABLE 4

|  |  |  | Comparative example 1 | Comparative example 2 | Comparative example 3 | Comparative example 4 | Comparative example 5 | Comparative example 6 |
|---|---|---|---|---|---|---|---|---|
| First paste | Polymerization Catalyst | Cumene hydroperoxide |  |  |  |  | 1 | 1 |
|  |  | BPO | 1 | 1 |  |  |  |  |
|  |  | DAC |  |  | 1 | 5 |  |  |
|  | Polymer of α-β unsaturated monocarboxylic acid or α-β unsaturated dicarboxylic acid | Polycarboxylic acid | 34 | 34 | 20 | 20 | 20 | 20 |
|  | Water |  | 65 | 65 | 35 | 35 | 35 | 35 |
|  | Filler | Crystalline quartz |  |  | 40 | 36 |  |  |
|  |  | Amorphosized quartz |  |  |  |  | 40 | 40 |
|  |  | Aerosil |  |  | 4 | 4 | 4 | 4 |

TABLE 5

|  |  |  | Comparative example 1 | Comparative example 2 | Comparative example 3 | Comparative example 4 | Comparative example 5 | Comparative example 6 |
|---|---|---|---|---|---|---|---|---|
| Second Paste | Polymerization Catalyst | N-Acetylthiourea |  |  |  |  | 0.25 | 0.5 |
|  |  | p-Amine | 1 | 1 |  |  |  |  |
|  |  | N-C5EPT |  |  | 1 | 1 |  |  |
|  |  | AACu |  |  | 0.05 | 0.15 |  | 0.15 |
|  | (Meth)acrylate | UDMA | 4 | 4 | 4 | 4 | 3 | 3 |

TABLE 5-continued

|  |  | Comparative example 1 | Comparative example 2 | Comparative example 3 | Comparative example 4 | Comparative example 5 | Comparative example 6 |
|---|---|---|---|---|---|---|---|
|  | TEGDMA | 4 | 4 | 4 | 4 | 3 | 3 |
|  | HEMA | 20 | 20 | 20 | 20 | 20 | 20 |
| Filler | FG I | 65 | 65 |  |  |  |  |
|  | FG II |  |  | 65 | 65 | 69 | 69 |
|  | Aerosil | 5.8 | 5.8 | 5.75 | 5.65 | 4.55 | 4.15 |
| Other | Camphorquinone | 0.2 | 0.2 | 0.2 | 0.2 | 0.2 | 0.2 |

TABLE 6

|  |  |  | Example 1 | Example 2 | Example 3 | Example 4 | Example 5 | Example 6 |
|---|---|---|---|---|---|---|---|---|
| Preservation Stability [min.:sec.] | 23° C. | At a time of producing | 5:00 | 4:00 | 6:30 | 5:30 | 6:00 | 5:00 |
|  |  | After 12 weeks | 5:15 | 4:30 | 6:45 | 6:00 | 6:15 | 5:00 |
|  | 50° C. | At a time of producing | 5:00 | 4:00 | 6:30 | 5:30 | 6:00 | 5:00 |
|  |  | After 12 weeks | 5:45 | 4:30 | 7:00 | 6:00 | 7:00 | 5:30 |

TABLE 7

|  |  |  | Comparative example 1 | Comparative example 2 | Comparative example 3 | Comparative example 4 | Comparative example 5 | Comparative example 6 |
|---|---|---|---|---|---|---|---|---|
| Preservation Stability [min.:sec.] | 23° C. | At a time of producing | Not cured | 10:00 | 10:00 | 8:30 | 8:30 | 7:30 |
|  |  | After 12 weeks | Not cured | 12:00 | 13:00 | Could not measure | 12:00 | 11:00 |
|  | 50° C. | At a time of producing | Not cured | 10:00 | 10:00 | 8:30 | 8:30 | 7:30 |
|  |  | After 12 weeks | Not cured | 13:30 | 14:00 | Could not measure | Not cured | 13:00 |

What is claimed is:

1. A polymerizable composition, comprising a first paste and a second paste,
wherein:
the first paste comprises a polymer of α-β unsaturated monocarboxylic acid or α-α unsaturated dicarboxylic acid, water, and a hydroperoxide as a peroxide;
the second paste comprises a (meth)acrylate compound not having an acid group, fluoroaluminosilicate glass powder, a thiourea compound as a reducing material, and a vanadium compound as a polymerization accelerator; and
the polymer does not include a polymerizable ethylenic unsaturated double bond, and has a weight-average molecular weight of 5,000 to 40,000.

2. The composition of claim 1, wherein the thiourea compound is at least one selected from the group consisting of ethylenethiourea, diethylthiourea, tetramethylthiourea, N-acetylthiourea, N-benzoylthiourea, diphenylthiourea, and dicyclohexylthiourea.

3. The composition of claim 1, wherein the vanadium compound is at least one selected from the group consisting of vanadium acetylacetonate, vanadyl acetylacetonate, vanadyl stearate, vanadium naphthenate, and vanadium benzoyl acetonate.

4. The composition of claim 2, wherein the vanadium compound is at least one selected from the group consisting of vanadium acetylacetonate, vanadyl acetylacetonate, vanadyl stearate, vanadium naphthenate, and vanadium benzoyl acetonate.

5. The composition of claim 1, wherein the first paste comprises a polymer of at least one α-β unsaturated monocarboxylic acid selected from the group consisting of acrylic acid, methacrylic acid, 2-chloroacrylic acid and 3-chloroacrylic acid.

6. The composition of claim 1, wherein the first paste comprises a polymer of at least one α-β unsaturated dicarboxylic acid selected from the group consisting of aconitic acid, mesaconic acid, maleic acid, itaconic acid, fumaric acid, glutaconic acid and citraconic acid.

7. The composition of claim 1, wherein a blending amount of the polymer is 10 to 60% be weight of the first paste.

8. The composition of claim 1, wherein a blending amount of the water is 10 to 60% by weight of the first paste.

9. The composition of claim 1, wherein a blending amount of the hydroperoxide in the first paste is 0.01 to 10% by weight of the first paste.

10. The composition of claim 1, wherein the hydroperoxide is at least one selected from the group consisting of p-methane hydroperoxide, diisopropylbenzene hydroperoxide, 1,1,3,3-butyl hydroperoxide, cumene hydroperoxide and tert-butyl hydroperoxide.

11. The composition of claim 1, wherein the (meth)acrylate compound is at least one selected from the group consisting of methyl(meth)acrylate, ethyl(meth)acrylate, isopropyl(meth)acrylate, n-butyl(meth)acrylate, isobutyl(meth)acrylate, hydroxypropyl(meth)acrylate, tetrahydrofurfryl (meth)acrylate, glycidyl(meth)acrylate, 2-hydroxyethyl (meth)acrylate, 2-hydroxypropyl(meth)acrylate, 3-hydroxypropyl(meth)acrylate, 2-methoxyethyl(meth) acrylate, 2-ethoxyethyl(meth)acrylate, 2-methoxyethyl (meth)acrylate, 2-ethylhexyl(meth)acrylate, benzyl(meth) acrylate, 2-hydroxy-1,3-di(meth)acryloxy propane, ethylene glycol di(meth)acrylate, diethylene glycol di(meth)acrylate, triethylene glycol di(meth)acrylate, butylene glycol di(meth) acrylate, neopentyl glycol di(meth)acrylate, 1,3-butanediol di(meth)acrylate, 1,4-butanediol di(meth)acrylate, 1,6-hexanediol di(meth)acrylate, trimethylolpropane tri(meth)acrylate, trimethylolethane tri(meth)acrylate, pentaerythritol tri (meth)acrylate, trimethylolmethane tri(meth)acrylate, pentaerythritol tetra(meth)acrylate, polybutyle glycol di(meth)acrylate, di-2-(meth)acryloxyethyl-2,2,4-trimethylhexamethylene dicarbamate, 1,3,5-tris[1,3-bis ((meth)acryloyloxy)-2-propoxycarbonylaminohexane]-1,3,5-(1H,3H,5H)triazine-2,4,6-trione, 2,2-bis-4-(3-(meth)acryloyloxy-2-hydroxypropyl)-phenylpropane, and a (meth)acrylate of a urethane oligomer.

12. The composition of claim 1, wherein the fluoroaluminosilicate glass powder comprises 10 to 21% by weight of $Al^{3+}$, 9 to 21% by weight of $Si^{4+}$, 1 to 20% by weight of $F^-$, and 10 to 34% by weight of $Sr^{2+}$, $Ca^{2+}$, or both, with respect to a total weight of the fluoroaluminosilicate glass powder.

13. The composition of claim 12, wherein the fluoroaluminosilicate glass power is treated with a silane coupling agent.

14. The composition of claim 1, wherein a content of the thiourea compound is 0.01 to 10% by weight of the second paste.

15. The composition of claim 1, wherein a content of the vanadium compound is 0.001 to 1% by weight of the second paste.

16. The composition of claim 1, further comprising a filler other than the fluoroaluminosilicate glass powder.

17. The composition of claim 16, wherein the filler is at least one selected from the group consisting of anhydrous silicic acid, hydrous silicic acid, hydrous calcium silicate and hydrous aluminum silicate.

18. The composition of claim 17, wherein the filler is treated with a silane coupling agent.

19. The composition of claim 18, wherein the silane coupling agent is at least one selected from the group consisting of γ-methacryloxypropyltrimethoxysilane, vinyltrichlorosilane, vinyltrimethoxysilane, vinyltriethoxysilane, vinyltriacetoxysilane, and vinyltri(methoxyethoxy)silane.

20. A polymerizable composition, comprising a first paste and a second paste, wherein:
the first paste comprises a polymer of α-β unsaturated monocarboxylic acid or α-β unsaturated dicarboxylic acid, water, and a hydroperoxide as a peroxide;
the second paste comprises a (meth)acrylate compound not having an acid group, fluoroaluminosilicate glass powder, a thiourea compound as a reducing material, and a vanadium compound as a polymerization accelerator; and
a blending amount of the water is 10 to 60% by weight of the first paste.

* * * * *